(12) United States Patent
Frerichs et al.

(10) Patent No.: US 8,056,394 B2
(45) Date of Patent: Nov. 15, 2011

(54) PROCEDURE FOR MEASURING THE CONCENTRATION OF A GAS

(75) Inventors: Heinz-Peter Frerichs, St. Peter (DE); Hans-Günter Zimmer, Reute (DE); Tobias Kolleth, Freiburg (DE); Christoph Wilbertz, Gundelfingen (DE)

(73) Assignee: Micronas GmbH, Freiburg (DE)

( * ) Notice: Subject to any disclaimer, the term of this patent is extended or adjusted under 35 U.S.C. 154(b) by 462 days.

(21) Appl. No.: 12/411,132

(22) Filed: Mar. 25, 2009

(65) Prior Publication Data

US 2009/0272175 A1    Nov. 5, 2009

(30) Foreign Application Priority Data

Mar. 26, 2008   (EP) .................................... 08005559

(51) Int. Cl.
*G01N 25/00* (2006.01)
(52) U.S. Cl. ..................................... 73/25.01
(58) Field of Classification Search .................... 374/45; 73/25.01
See application file for complete search history.

(56) References Cited

U.S. PATENT DOCUMENTS

| | | | | | |
|---|---|---|---|---|---|
| 3,716,337 | A | * | 2/1973 | Jones | 422/88 |
| 4,063,898 | A | * | 12/1977 | Fisher | 422/94 |
| 4,541,988 | A | * | 9/1985 | Tozier et al. | 422/94 |
| 5,573,728 | A | * | 11/1996 | Loesch et al. | 422/90 |
| 5,897,836 | A | * | 4/1999 | Martell et al. | 422/90 |
| 6,644,098 | B2 | * | 11/2003 | Cardinale et al. | 73/25.01 |
| 6,812,708 | B2 | * | 11/2004 | Bristol | 324/431 |
| 6,843,100 | B2 | * | 1/2005 | Bair et al. | 73/23.2 |
| 2003/0039299 | A1 | * | 2/2003 | Horovitz et al. | 374/141 |
| 2008/0098799 | A1 | * | 5/2008 | Kirk et al. | 73/25.01 |

FOREIGN PATENT DOCUMENTS

| | | |
|---|---|---|
| DE | 4333875 A1 | 4/1995 |
| EP | 1879023 A1 | 1/2008 |

OTHER PUBLICATIONS

Galonska, T. et al., "Cross Sensitivity and Stability of FET—Based Hydrogen Sensors", IEEE Senors (2007), pp. 1036-1039, Department of Physics, University of the Federal Armed Forces, Munich, Germany.

Burgmair, M. et al., "Humidity and temperature compensation in work function gas sensor FETs", Sensors and Actuators, vol. B, No. 93, (2003), pp. 271-275, Institute of Physics, Neubiberg, Germany.

* cited by examiner

*Primary Examiner* — Hezron E Williams
*Assistant Examiner* — Nathaniel Kolb
(74) *Attorney, Agent, or Firm* — Muncy, Geissler, Olds & Lowe, PLLC

(57) ABSTRACT

In a procedure for measuring the concentration of a target gas, a gas sensor is provided whose sensor signal at constant temperature is dependent on a target gas concentration and has a lower measurement sensitivity in a first modulation range than in a second modulation range. The position of the modulation ranges is dependent on the temperature. The temperature of the gas sensor is controlled so that the sensor signal is essentially independent of the target gas concentration and lies within the second modulation range. The temperature of the gas sensor is then a measurement for the target gas concentration.

12 Claims, 6 Drawing Sheets

PROCEDURE FOR MEASURING THE CONCENTRATION OF A GAS

Figure 1:
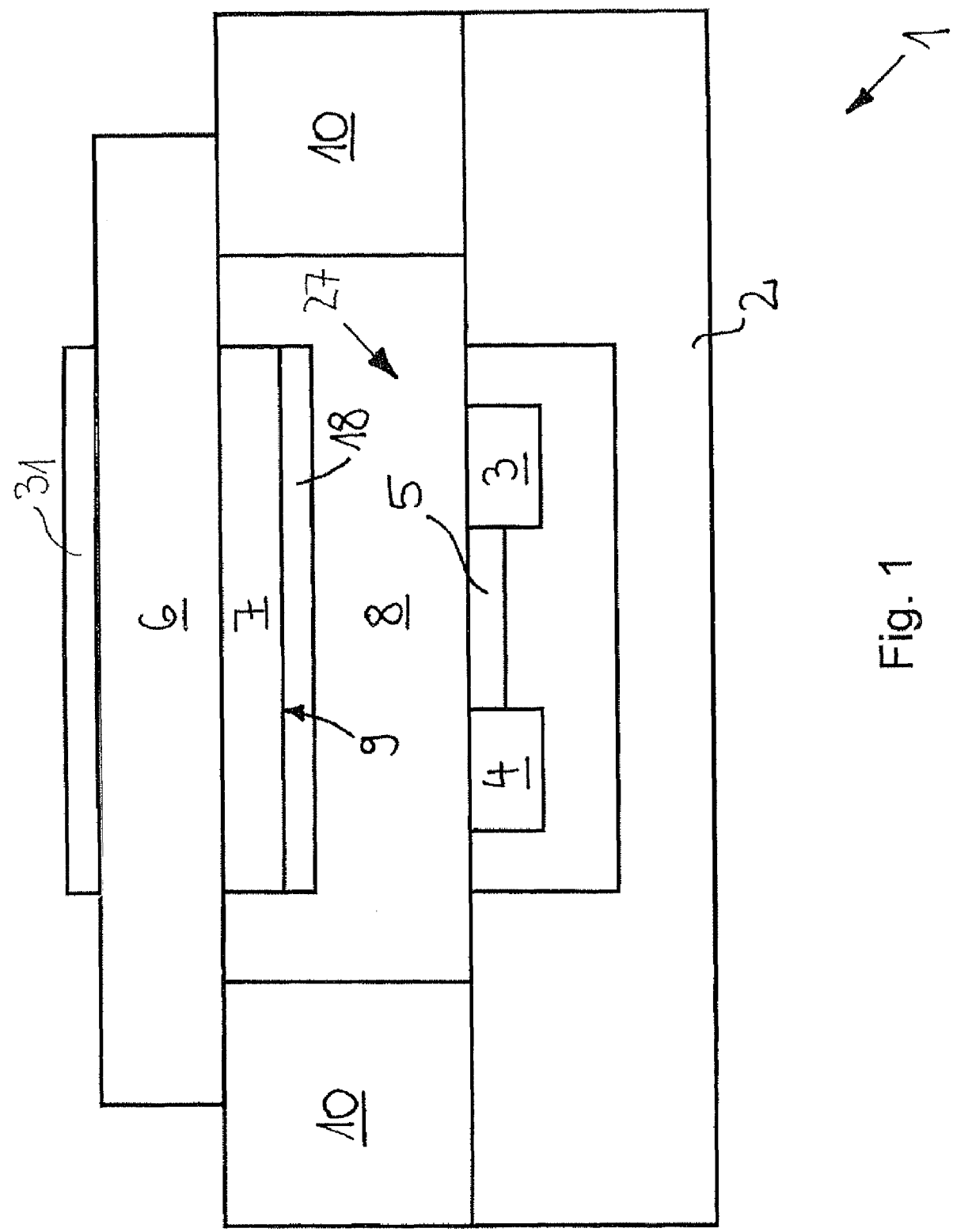

The invention relates to a procedure for measuring the concentration of a target gas, wherein a gas sensor is provided whose sensor signal is dependent on a target gas concentration.

Such a procedure is disclosed in DE 43 33 875 C2. With this procedure, a gas sensor is provided which has a silicon substrate in which a field effect transistor is integrated. The field effect transistor has a gate electrode which is conductively connected to a sensor electrode, over which is arranged a gas sensitive layer, which gas sensitive layer is separated from the sensor electrode and capacitively coupled to the sensor electrode by an air gap. A cover electrode is mounted on the back side of the gas sensitive layer facing away from the sensor electrode. A surface zone of the gas sensitive layer facing towards the sensor electrode is brought into contact with a target gas, which is adsorbed on the surface zone upon contact therewith. With a change in the concentration of the target gas, the electron affinity in the surface zone of the gas sensitive layer changes. Because the sensor electrode is capacitively coupled to the surface zone, the electric potential on the gate electrode also changes. The current flow between a drain connector and a source connector of the field effect transistor is controlled as a function of the change in potential. In such a gas sensor the measurement signal is approximately logarithmic to the target gas concentration, i.e., the measurement sensitivity decreases as the target gas concentration increases. Because the presence of oxygen may also interfere with the measurement signal, the measurement of higher target gas concentrations with this procedure is problematic.

The object is therefore to provide a procedure for measuring the concentration of a target gas that enables a high measurement precision.

This object is achieved by provision of a gas sensor whose sensor signal at a constant temperature is dependent on the target gas concentration and which has a lower measurement sensitivity in a first modulation range than in a second modulation ranger wherein the gas concentrations allocated to the modulation ranges are dependent on the temperature, and wherein the temperature of the gas sensor is controlled so that the sensor signal is essentially independent of the target gas concentration and lies within the second modulation range, and wherein the temperature of the gas sensor is a measurement for the target gas concentration.

With different target gas concentrations, the working point of the gas sensor is thus advantageously always located in the modulation range with the greater measurement sensitivity, whereby different target gas concentrations can be measured with the same measurement sensitivity. The temperature control is thus effected so that, with a change in the target gas concentration, the sensor signal of the gas sensor more or less maintains its value, so that the target gas concentration can then be determined from the set temperature. The modulation ranges can be experimentally measured and/or determined beforehand with the aid of a mathematical model.

In a preferred embodiment of the invention, the temperature is controlled so that the gas sensor is operated at a working point at which the gas sensor has its greatest sensitivity to the target gas. An even more precise measurement of the target gas concentration is then possible.

It is advantageous if the controlling of the temperature of the gas sensor takes place only if the detected temperature lies within a prespecified temperature range, and if the concentration of the target gas is determined outside this temperature range as a function of the sensor signal of the gas sensor and parameters. In a target gas concentration range in which the gas sensor still has sufficient measurement accuracy even without temperature control and/or in which controlling the temperature of the gas sensor is too complex, the temperature control can thus be deactivated. In this way the procedure can be carried out more easily and with less energy expenditure.

In a preferred embodiment of the invention, the temperature outside the temperature range provided for the temperature control is set to a constant temperature value. Measurement inaccuracies caused by fluctuations in ambient temperature while the temperature control is deactivated can thus be avoided.

It is advantageous if the temperature range provided for the temperature control lies above 60° C., particularly above 70° C., and where appropriate above 80° C. The temperature of the gas sensor is then easily adjustable by heating.

The sensor signal is advantageously captured by measuring the electron affinity of a gas sensitive layer. Preference is given to the gas sensitive layer being covered with an electrically insulating coating that is inert to the target gas, adhesively bound to the gas sensitive layer, and configured so that it is permeable to the target gas whose concentration is to be measured and another gas differing from the target gas and capable of being adsorbed on the surface zone. The coating can have different diffusion constants for the target gas and the other gas, wherein the diffusion constants, the target gas, and the other gas are selected with respect to each other so that the sensitivity of the gas sensor to the target gas increases if the target gas concentration exceeds a prespecified concentration threshold in the absence of the other gas.

Preference is given to the sensor signal being capacitively measured across an air gap on the gas sensitive layer. In the procedure of the invention, however, the sensor signal can also be captured by measuring the electrical resistance of the gas sensitive layer. For doing so, the gas sensitive layer can be a metallic oxide layer which changes its resistance upon exposure to gas.

In an advantageous embodiment of the invention, the temperature of the gas sensor is adjusted to a target temperature which is higher than the ambient temperature of the gas sensor, wherein the gas sensor is heated in order to set the target temperature. The gas sensor can then be operated in the second modulation range also at low ambient temperatures.

In another advantageous embodiment of the invention, the temperature of the gas sensor is adjusted to a target temperature which is lower than the ambient temperature of the gas sensor, wherein the gas sensor is cooled to set the target temperature. With cooling, it is possible to operate the gas sensor at a target temperature enabling a high measurement precision and/or measurement resolution, even at high ambient temperatures such as the ones that can occur in the engine compartment of a motor vehicle with an internal combustion engine.

Figure 2:
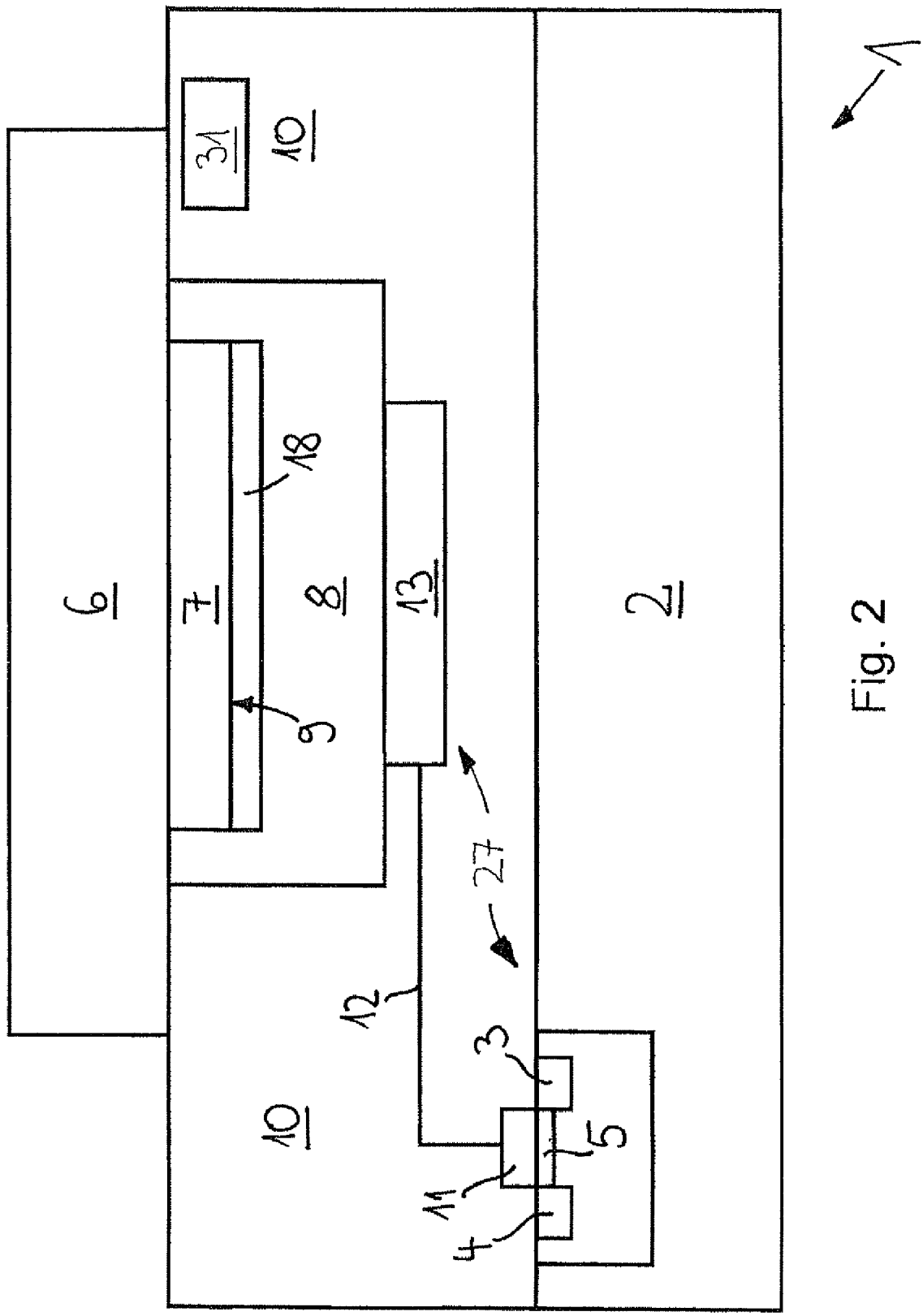
Figure 3:
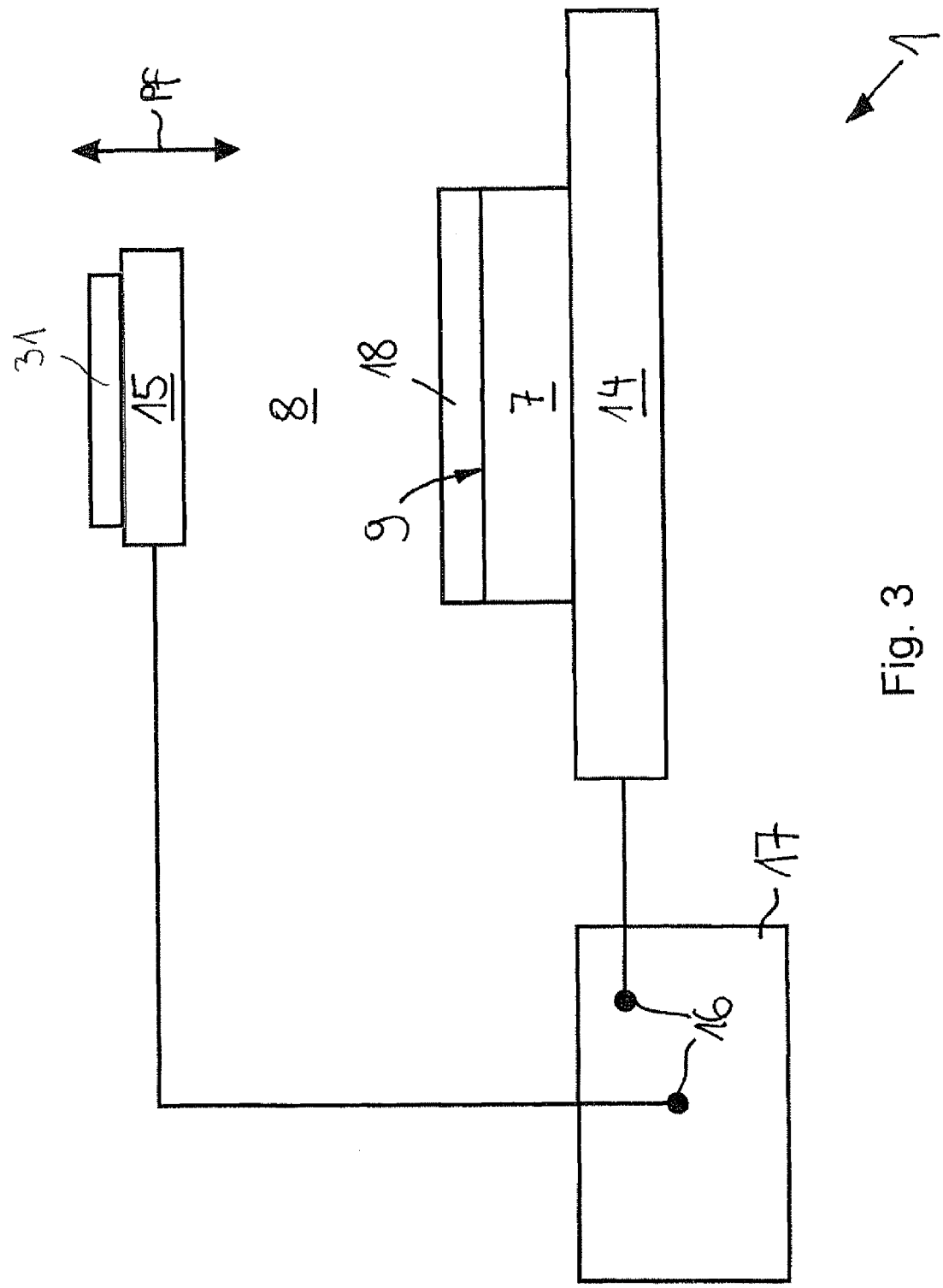
Figure 4:
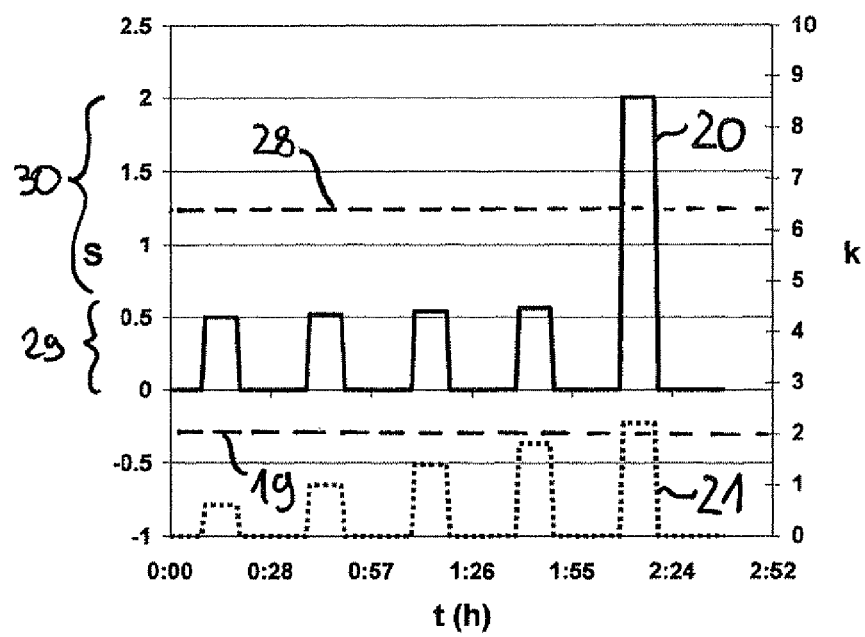
Figure 5:
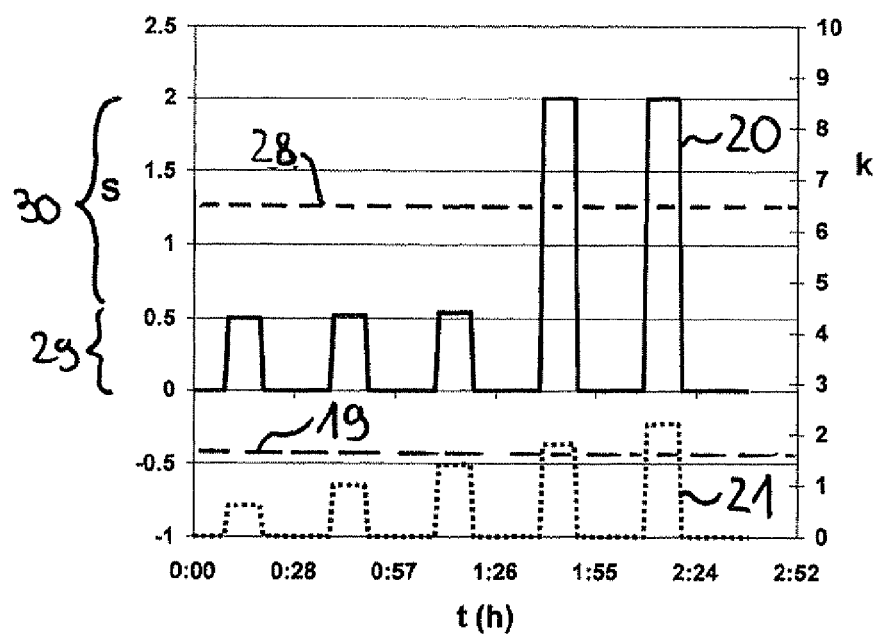
Figure 6:
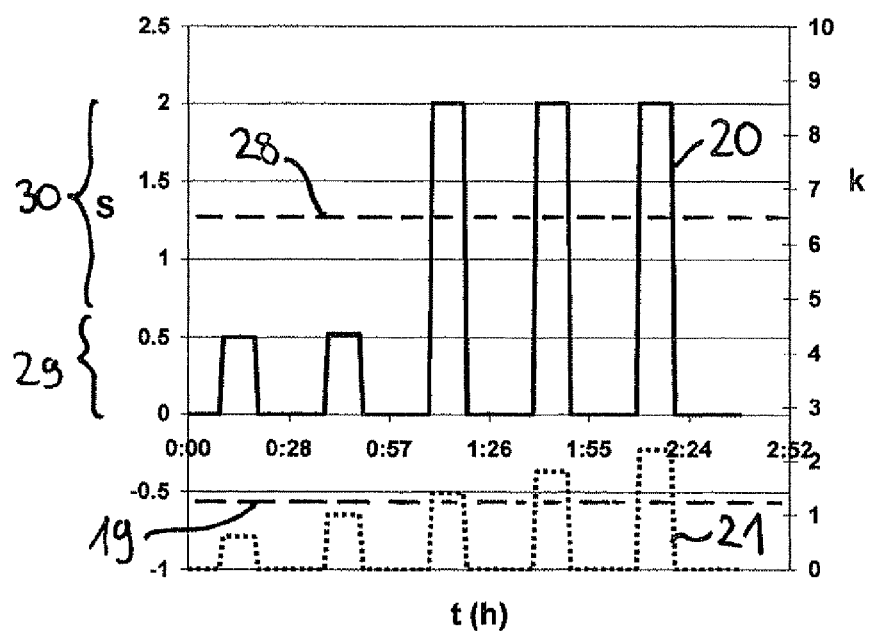
Figure 7:
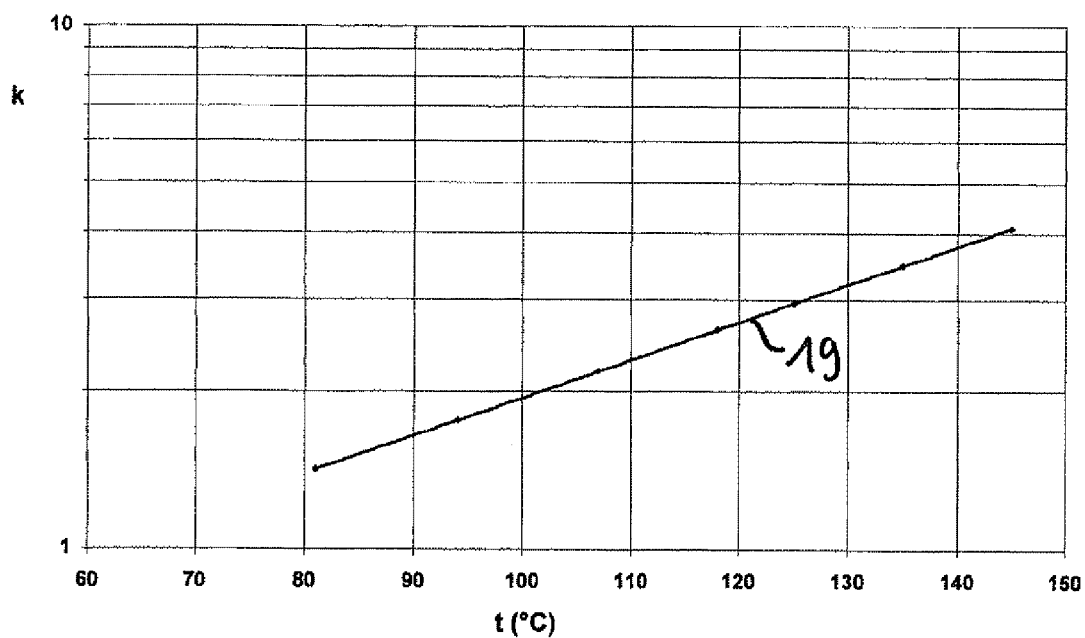
Figure 8:
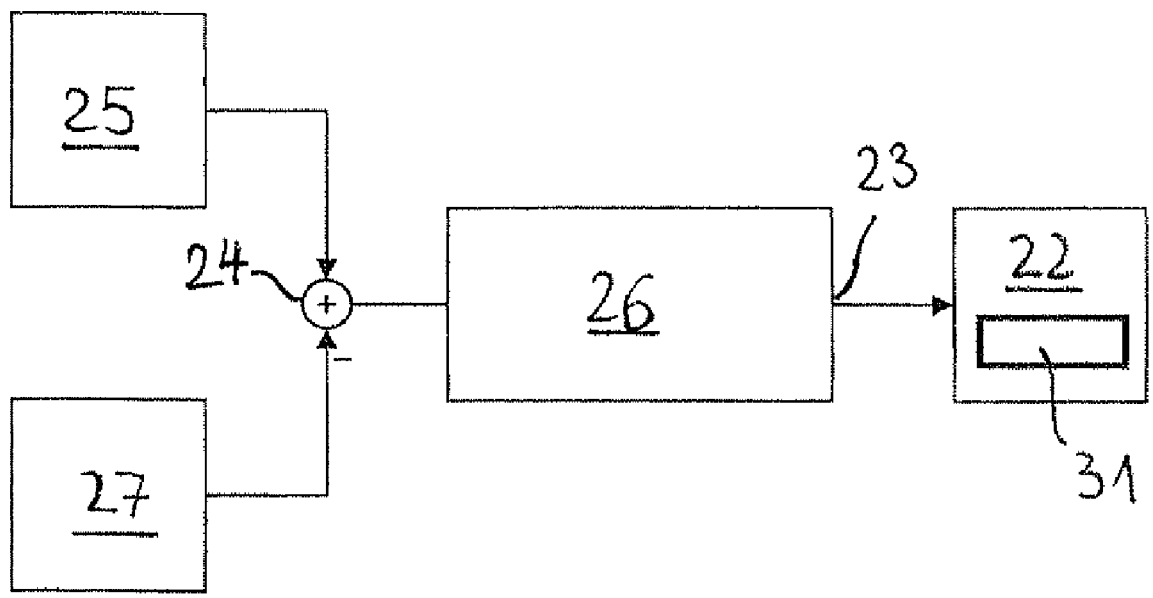

Illustrative embodiments of the invention are explained in greater detail in the following, with reference to the drawing. Shown are:

FIG. 1 a cross-section of a gas sensor, which has a SGFET, whose channel zone is capacitively coupled by an air gap to a gas sensitive layer provided with a passivation coating, FIG. 2 a cross-section of a gas sensor, which has a CCFET, whose sensor electrode is capacitively coupled by an air gap to a gas sensitive layer provided with a passivation coating, FIG. 3 a cross-section of a gas sensor configured as a Kelvin probe, in which the gas sensitive layer has a passivation coating, FIG. 4 a graphic illustration of a sensor signal (top curve) and the target gas concentration (bottom curve) of an illustrative embodiment of the gas sensor, wherein the time t is graphed on the abscissa and the amplitude S of the sensor signal of an electric potential sensor is graphed on the left ordinate and the target gas concentration k is graphed on the right ordinate, FIG. 5 an illustration similar to FIG. 4, wherein, however, the temperature of the gas sensor is less than that in FIG. 4, FIG. 6 an illustration similar to FIG. 5, wherein, however, the temperature of the gas sensor is less than that in FIG. 5, FIG. 7 a graphic illustration of a threshold for the target gas concentration of the gas sensor, wherein the temperature is graphed on the abscissa and the threshold is graphed on the ordinate, and FIG. 8 a schematic illustration of a control mechanism.

In a procedure for measuring the concentration of a target gas, a gas sensor 1 configured as a SGFET, as a CCFET, or as a Kelvin probe is provided.

As can be discerned in FIG. 1, the gas sensor configured as a SGFET has a substrate 2 in which an electric potential sensor 27 is integrated. The electric potential sensor 27 has a drain 3 and a source 4, which are arranged in an n-doped transistor tub. The drain 3 and the source 4 can be composed of, for example, p-doped silicon. The drain 3 is connected via electrical conductor paths to a drain connector, which is not shown in any greater detail in the drawing. In an analogous manner the source 4 is connected to a source connector. A channel zone 5 on which is arranged an electrically insulating thin oxide layer serving as a gate dielectric is formed in the substrate 2 between the drain 3 and the source 4.

A gas sensitive layer 7, which is preferably composed of a noble metal, particularly platinum or palladium, is arranged on a mounting element 6 above the channel zone 5 and separated from said channel zone 5 by an air gap 8. A surface zone 9 of the gas sensitive layer 7 facing towards the channel zone 5 is capacitively coupled by the air gap 8 to said channel zone 5.

The mounting element 6 is connected to the substrate 2 on both sides of the gas sensitive layer 7 via an electrical insulation layer 10. It is clearly discernible in FIG. 1 that the mounting element 6 and the gas sensitive layer 7 form a suspended gate.

The air gap 4 is connected to the atmosphere surrounding the gas sensor 1 by at least one opening, which is not shown in any greater detail in the drawing. The surface zone 9 of the gas sensitive layer 7 is brought into contact via this opening with a target gas to be detected, namely hydrogen, and another gas, namely an electronegative gas, for example atmospheric oxygen. Upon contact with the surface zone 9, the target gas and the other gas are adsorbed on the surface zone 9. Upon adsorption of the target gas, the electron affinity in the surface zone 9 changes, which leads to a change of the electric potential in the channel zone 5.

In the illustrative embodiment according to FIG. 1, the channel zone 5 is configured as an open channel (ISFET) and capacitively coupled directly to the gas sensitive layer 7 by the thinlayer oxide and the air gap 8. It is clearly discernible that the channel zone 5 is arranged on the side of the air gap 8 positioned opposite to the gas sensitive layer 7.

In the illustrative embodiment according to FIG. 2, the field effect transistor is configured as a CCFET in which the channel zone 5 is laterally positioned to the gas sensitive layer 7 in the substrate 2 and capped with a gate electrode 11. To capacitively couple the channel zone 5 to the gas sensitive layer 7, the gate electrode 11 is connected via an electrical connecting line 12 to a sensor electrode 13, which is arranged on an insulation layer 10 on the substrate 2 on the side of the air gap 8 positioned opposite to the surface zone 9 of the gas sensitive layer 7. The insulation layer 10 can be, for example, a $SiO_2$ layer. The configuration of the suspended gate of the SGFET corresponds to that in FIG. 1.

In the illustrative embodiment shown in FIG. 3, the gas sensor 1 is configured as a Kelvin probe. The gas sensitive layer 7 is arranged on an electrically conductive mount 14 and has on its side facing away from the mount 14 a surface zone 9, on which the target gas can be adsorbed. The surface zone 9 is separated by an air gap 8 from an electrode 15, with which it forms an electrical capacity.

The electrode 15 can be set into oscillation by an actuator, which is not shown in any greater detail in the drawing. The electrode 15 thus moves alternately towards and away from the gas sensitive layer 7, as indicated by the arrow Pf. The electrode 15 and the mount 14 or the gas sensitive layer 7 are connected to connectors 16 of an evaluation and modulation device 17. The latter has an electric potential sensor (not shown in any greater detail), which is connected to the connectors 16 for measuring the voltage between the gas sensitive layer 7 and the electrode 15. The evaluation and modulation device 17 also has an adjustable voltage source which is control-connected to the electric potential sensor, and via which a countervoltage is applied between the electric potential sensor and the electrode 15 and/or the mount 15. The countervoltage is selected so that the electric potential measured by the electric potential sensor in the center is equal to zero.

In the gas sensors 1 described above, the surface zone 9 of the gas sensitive layers 7 is always continuously covered by an electrically insulating polymer coating 18, which is inert to the target gas and which is preferably composed of polymethylmethacrylate (PMMA) or polyimide. The coating 18 adheres tightly to the gas sensitive layer 7. The coating 18 is configured as a thick layer with an approximately constant thickness, which preferably measures between 0.5 µm and 2.5 µm.

The coating 18 is permeable to the target gas as well as to the other gas. The diffusion constants, the target gas, and the other gas are adapted to each other so that the sensitivity of the gas sensor 1 to the target gas strongly increases when the concentration of the target gas exceeds a threshold 19 in the absence of the other gas. The position of the threshold 19 is dependent on the temperature.

It can be discerned in FIGS. 4-6 that, at constant temperature and target gas concentrations 21 lying within a first concentration range whose upper limit is delineated by the concentration threshold 19, the sensor signal 20 of the electric potential sensor 27 always at first increases approximately logarithmically with the target gas concentration 21. In the first concentration range, the sensor signal 20 of the electric potential sensor 27 lies within a first modulation range 29.

In a second concentration range, which at its lower end borders the concentration threshold and is considerably narrower than the first concentration range, the sensor signal 20 strongly increases at constant temperature. In the second concentration range, the sensor signal 20 lies within a second modulation range 30, in which the measurement sensitivity of the gas sensor 1 is greater than in the first modulation range 29. In a third concentration range, which lies above the second concentration range and borders it, the sensor signal 20 of the electric potential sensor 27 at constant temperature remains essentially constant at a value bordering the second concentration range.

In FIG. 7 it can be discerned that the concentration threshold 19 is dependent on the temperature of the layer sequence formed from the gas sensitive layer 7 and the coating 18 and continuously increases with increasing temperature. The increase is approximately exponential to the temperature. Where appropriate, the exponential increase can be linearly approximated in the relevant range for the concentration measurement.

The gas sensors illustrated in FIGS. 1-3 in each case have a thermostat 22, which is only schematically illustrated in FIG. 8, by means of which the temperature of the gas sensitive layer 7 and the coating 18 is adjustable. A control input of the thermostat 22 is connected to a control signal output 23 of a control mechanism, which is used to adjust the temperature of the gas sensitive layer 7 and the coating 18 so that the sensor signal 20 of the electric potential sensor 27 is always essentially independent of the target gas concentration 21 and lies within the second modulation range 30.

The thermostat 22 can comprise a heating and/or a cooling element 31, which, for example, can be arranged on or integrated in the mounting element 6. In the illustrative embodiment shown in FIG. 1, the heating and/or cooling element 31 is mounted on the back side of the mounting element 6 facing away from the gas sensitive layer 7. The heating and/or cooling element 31 can comprise a Peltier element and/or an electrical resistance heater.

It can be discerned in FIG. 2 that the heating and/or cooling element 31 can also be arranged on or integrated in the insulation layer 10. The heating and/or cooling element 31 is arranged on the electrode 15 in the illustrative embodiment shown in FIG. 3.

The control mechanism has a comparator 24, which has an actual value input connected to the electric potential sensor 27 and a target value input connected to a director 25. An output of the comparator 24 is connected via a modulator 26 to the control signal output 23. By means of the director 25, a target value 28 is applied to the target value input, which lies within the second modulation range 30 and thus corresponds to a value that the sensor signal 20 of the electric potential sensor 27 has at a target gas concentration 21 above the concentration threshold 19.

In a first operating mode of the gas sensor 1, the modulator 26 always controls the thermostat 22 so that in the event of a deviation between the sensor signal 20 of the electric potential sensor 27 and the target value 28, the temperature of the gas sensitive layer 7 and the coating 18 is changed so as to reduce the deviation. If the sensor signal 20 of the electric potential sensor 27 coincides with the target value 28, the temperature of the gas sensitive layer 7 and the coating 18 is a measurement for the target gas concentration 21.

In a second operating mode, the temperature of the gas sensitive layer 7 and the coating 18 is set to a constant value with the thermostat 22. Alternately, the thermostat 22 can also be deactivated in the second operating mode, so that the temperature of the gas sensor 1 then corresponds approximately to the ambient temperature. The second operating mode is always activated when the temperature detected by the modulator 26 falls below a prespecified minimum temperature value. This value can be, for example, ca. 60-80° C.

In the second operating mode the target gas concentration 21 is determined as a function of the signal value of the sensor signal 20 of the electric potential sensor 27 and as a function of parameters, which can be in the form of, for example, a characteristic line. In the second operating mode the signal analysis is essentially analogous to that of a standard gas sensor. As soon as the minimum temperature value is exceeded, the sensor switches to the first operating mode, in order to determine the target gas concentration 21 as a function of the set temperature. The first operating mode is thus used for higher target gas concentrations 21 and the second operating mode for lower target gas concentrations 21.

Preference is given to selection of the first operating mode if the concentration of the target gas is between 1% and 4%. The corresponding concentration range can be determined experimentally. In this range there is an approximately exponential correlation between the temperature and the target gas concentration 21. Compared with a standard gas sensor, the gas sensor 1 of the invention thus enables a considerably better resolution in this concentration range.

The invention claimed is:

1. A procedure for measuring the concentration of a target gas, the steps comprising:
   providing a gas sensor whose sensor signal at constant temperature is dependent on a target gas concentration and has a lower measurement sensitivity in a first modulation range than in a second modulation range, wherein the gas concentrations allocated to the modulation ranges are dependent on the temperature;
   controlling the temperature of the gas sensor so that the sensor signal is essentially independent of the target gas concentration and lies within the second modulation range; and
   using the temperature of the gas sensor as a measurement for the target gas concentration.

2. The procedure as in claim 1, wherein the temperature is controlled so that the gas sensor is operated at a working point at which the gas sensor has its greatest sensitivity to the target gas.

3. The procedure as in claim 1, wherein the temperature of the gas sensor is only controlled when a target temperature detected for the gas sensor lies within a prespecified temperature range, and wherein the concentration of the target gas outside this temperature range is determined as a function of the sensor signal of the gas sensor and parameters.

4. The procedure as in claim 1, wherein the temperature outside the temperature range provided for the temperature control is set to a constant temperature value.

5. The procedure as in claim 1 wherein the temperature range provided for the temperature control lies above 60° C.

6. The procedure as in claim 1, wherein the sensor signal is captured by measuring the electron affinity of a gas sensitive layer.

7. The procedure as in claim 1, wherein the sensor signal is capacitively measured across an air gap on the gas sensitive layer.

8. The procedure as in claim 1, wherein the sensor signal is captured by measuring the electrical resistance of the gas sensitive layer.

9. The procedure as in claim 1, wherein the temperature of the gas sensor is adjusted to a target temperature which is higher than the ambient temperature of the gas sensor, and wherein the gas sensor is heated in order to reach the target temperature.

10. The procedure as in claim 1, wherein the temperature of the gas sensor is adjusted to a target temperature which is lower than the ambient temperature of the gas sensor, and wherein the gas sensor is cooled in order to reach the target temperature.

11. The procedure as in claim 1, wherein the temperature range provided for the temperature control lies above 70° C.

12. The procedure as in claim 1, wherein the temperature range provided for the temperature control lies above 80° C.

* * * * *